United States Patent
Preckel et al.

(10) Patent No.: US 7,096,710 B2
(45) Date of Patent: Aug. 29, 2006

(54) METHOD FOR MONITORING THE OPERATIONAL CAPABILITY OF A TRANSPORT DEVICE AND LIQUID TRANSPORT DEVICE

(75) Inventors: Hartwig Preckel, Hamburg (DE); Oliver Wendt, Hamburg (DE); Axel Ehlert, Hamburg (DE)

(73) Assignee: Evotec OIA AG, Hamburg (DE)

( * ) Notice: Subject to any disclaimer, the term of this patent is extended or adjusted under 35 U.S.C. 154(b) by 72 days.

(21) Appl. No.: 10/483,083

(22) PCT Filed: Jul. 6, 2002

(86) PCT No.: PCT/EP02/07554

§ 371 (c)(1),
(2), (4) Date: Jul. 6, 2004

(87) PCT Pub. No.: WO03/006998

PCT Pub. Date: Jan. 23, 2003

(65) Prior Publication Data

US 2004/0255641 A1    Dec. 23, 2004

(30) Foreign Application Priority Data

Jul. 9, 2001 (DE) .................................. 101 32 530

(51) Int. Cl.
*G01F 25/00* (2006.01)
(52) U.S. Cl. ........................................ 73/1.74
(58) Field of Classification Search ............ 73/1.74; 222/63, 148, 196, 198, 202, 203, 258, 401
See application file for complete search history.

(56) References Cited

U.S. PATENT DOCUMENTS

| | | |
|---|---|---|
| 5,838,350 A | 11/1998 | Newcombe et al. |
| 6,094,966 A | 8/2000 | Papen et al. |
| 6,112,605 A | 9/2000 | Papen et al. |
| 6,158,269 A | 12/2000 | Dorenkott et al. |

FOREIGN PATENT DOCUMENTS

| | | |
|---|---|---|
| DE | 4029616 A1 | 3/1992 |
| EP | 0 580 483 A1 | 1/1994 |
| GB | 2297312 A | 7/1996 |
| JP | 01-150549 | 6/1989 |
| JP | 11-125638 | 5/1999 |
| WO | WO 98/45205 | 10/1998 |
| WO | WO 00/33961 | 6/2000 |

OTHER PUBLICATIONS

PTO 06-311, English language translation of Japanese Patent Application HEI 1 [1989]-150549 published Jun. 13, 1989.*
Tomita Mitsuo, Dispensing Apparatus, Patent Abstracts of Japan, Publication No. 11125638, Published May 11, 1999.

(Continued)

*Primary Examiner*—Charles Garber
(74) *Attorney, Agent, or Firm*—Griffin & Szipl, P.C.

(57) ABSTRACT

In a method for monitoring the operability of a liquid delivery device such as a dispenser (10), a response signal of a liquid-transformer system consisting of a transformer (24) and a chamber (12) containing a liquid is compared with a reference value. Preferably, the reference value is determined when the liquid-transformer system is operative, i.e., non-disturbed. The response signal differs from the reference value if there are air bubbles in the chamber (12), for example. By comparing the response signal with the reference value, a correction step such as a cleaning cycle can be performed when a limit value is exceeded or fallen short of.

23 Claims, 4 Drawing Sheets

OTHER PUBLICATIONS

Figures 1, 2:
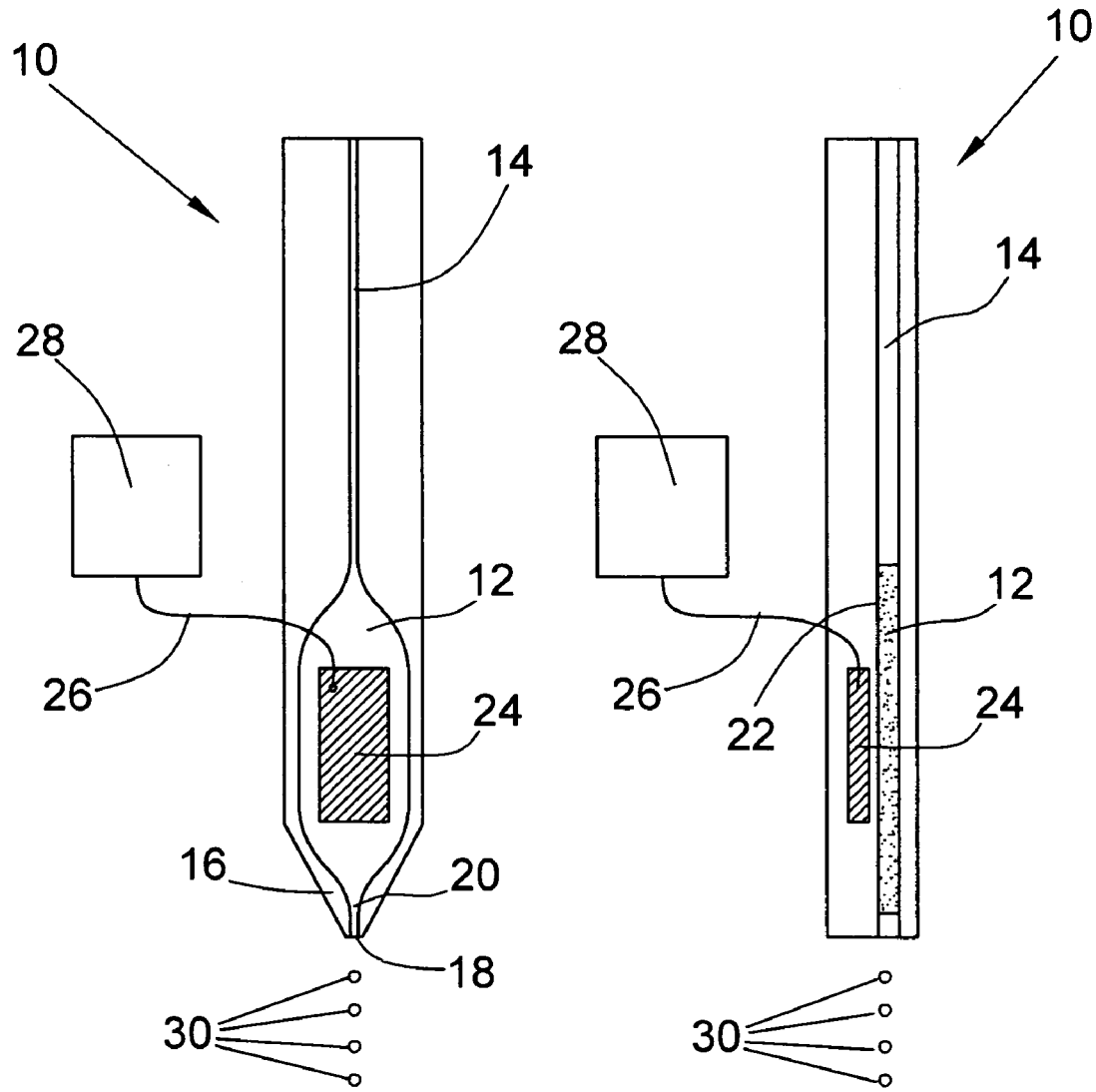

Koisumi Yukihisa, Bubble Detecting Device for Ink Flow Path in Ink Jet Printer, Patent Abstracts of Japan, Publication No. 01150549, Published Jun. 13, 1989.

International Search Report for International Application completed Feb. 5, 2003 and mailed Feb. 13, 2003, completed by C. Hanisch.

International Preliminary Examination Report for International Application in German.

English Language Translation of International Preliminary Examination Report for PCT/EP2002/007554, completed Oct. 28, 2003.

German Search Report, dated Apr. 12, 2002, 4 pages.

* cited by examiner

METHOD FOR MONITORING THE OPERATIONAL CAPABILITY OF A TRANSPORT DEVICE AND LIQUID TRANSPORT DEVICE

This is a National Phase Application in the United States of International Patent Application No. PCT/EP02/07554 filed Jul. 6, 2002, which claims priority on German Patent Application No. 101 32 530.4, filed Jul. 9, 2001. The entire disclosures of the above patent applications are hereby incorporated by reference.

The invention relates to a method for monitoring the operability of a liquid delivery device as well as to a liquid delivery device. Liquid delivery devices, for example, are pipetting or dispensing devices as well as pumps.

Dispensing and pipetting devices, for example, are used to fill sample carriers, such as, e.g., titer plates. Such titer plates comprise a plurality of wells, e.g., 1536 or 2080 wells, each well receiving a small quantity of sample liquid. Thereafter, the samples contained in the titer plates are analyzed in, e.g., automatic analysis processes such as the high throughput screening (HTS). A great number of samples is analyzed in a short time in high throughput screening installations in particular. Therefore, it is required to automatically fill the sample carriers with sample liquid.

Automatic dispensing or pipetting devices are employed to fill titer plates or other sample carriers. Such liquid delivery devices comprise a chamber for receiving liquid. Typically, the pressure in this chamber is increased to deliver liquid droplets. To this end, for example, a piezoelement is provided which acts upon the liquid provided in the chamber. Thus, liquid is delivered from a dispensing or pipetting tip by applying a voltage to the piezoelement. Sometimes, the delivered quantities for filling titer plates comprise only a few nanoliters, particularly less than 50 nl. For filling titer plates with a plurality of wells, several dispensing or pipetting devices are typically arranged next to each other and operated in parallel.

The micropumps, i.e., the combination of piezoelements and liquid chamber, are extremely susceptible to failure. Disturbances have an influence upon the liquid quantity delivered by the liquid delivery device. Particularly upon high throughput screening, even minor changes of the liquid quantity have a considerable influence upon the analysis results so that the analysis results are considerably falsified and thus become useless even with small liquid quantity deviations. Such disturbances, e.g., occur because of air bubbles in the chamber or capillaries connected to the chamber, from which the liquid is delivered or to which it is supplied. Further, depositions or efflorescences of or from the liquid may result in partial or complete cloggings. Disturbances may also be caused by liquid droplets at an outlet opening of the liquid delivery device since the flight direction of the drops is changed or the drops are not delivered at all. Disturbances may further occur as a result of changing physical properties of the liquid, such as, e.g., viscosity changes or changes of the composition of the liquid. Furthermore, disturbances may be caused by changing the ambience conditions, e.g., dipping the pipetting or dispensing tip into liquid.

It is the object of the invention to provide a method for monitoring the operability of a liquid delivery device by means of which the operability of the liquid delivery device is improved. Further, it is an object of the invention to provide a liquid delivery device with an improved operability.

This object is solved, according to the invention, with a method according to claim 1 and a device according to claim 19.

In a liquid delivery device with a liquid receiving portion and a transformer acting upon the liquid in the liquid receiving portion 12, e.g., an electromechanical transformer such as a piezoactuator, a response signal produced by a liquid-transformer system in operation is used, according to the invention, to perceive occurring disturbances such as air bubbles, cloggings and the like. The response signal may be, e.g., a current, voltage or charge signal. Either a signal directly emitted by the transformer or a signal obtained by a transform can be used as a response signal. The knowledge forming the basis of the invention consists in that a liquid-transformer system, i.e., a system substantially consisting of mechanical components of the transformer and of liquid onto which the transformer acts, comprises one or more characteristic "fluidic resonances". This means that at least a part of the mass of the liquid covibrates together with the mechanical components of the transformer and influences the vibrational properties in a characteristic manner. The response signal also includes, e.g., information on faults in fluidic partial systems of the liquid-transformer system. Particularly distinct changes occur at the resonance frequency (frequencies), wherein it is particularly possible to detect a frequency shift or attenuation. Characteristic changes of a response signal, however, can also be detected at other frequencies. In this case, e.g., the viscosity and the composition of the liquid onto which the transformer acts have to be considered as well.

Due to an inclusion of air, a clogging or changing physical properties of the liquid, e.g., the viscosity, the liquid-transformer system experiences a change of the vibrating mass. In other words, a response signal changes when the liquid-transformer system is excited by an excitation signal and a disturbance and/or change occurs. The response signal also changes when, e.g., the dispensing or pipetting tip, i.e., a delivering tip of the liquid delivery device, is dipped into liquid or a drop clings to the tip. Thereby, a part of the vibrations is transferred to the liquid into which the tip is dipped or the clinging drop increases the vibrating mass.

According to the method according to the invention, the transformer of the liquid-transformer system is excited by an excitation signal. This excitation is effected, for example, at regular time intervals during operation. At different times, different excitation signals can be used. Preferably, the excitation signal corresponds to a frequency of resonance. An excitation signal close to a frequency of resonance is also preferred. Preferably, the frequency difference between the frequency of resonance and the excitation signal is twice the half-width of the resonance at maximum. In the next step, the response signal of the liquid-transformer system caused by the excitation signal is acquired. Subsequently, the response signal is compared with a reference value. The reference value is, e.g., a preset value or a value stored in a control unit. The comparison between one or more reference values and a response signal can be made directly by means of an appropriate electronic circuit. It is also possible to compare and evaluate the signals in digitized form, respectively, with the use of software, if necessary. Because of a comparison of the response signal with the reference value, it can be decided whether a malfunction of the liquid delivery device is given. If this is true, a correction step is performed.

Preferably, the reference value is a response signal of the liquid-transformer system in which there are no disturbances such as cloggings and the like. This reference value, for example, may be stored in a memory means. Such a reference value is preferably determined by measuring the response signal of an operative liquid-transformer system at a frequency of resonance. This measurement can be performed once and then, the reference value is stored in the memory means. For checking purposes, a corresponding measurement can be repeated at regular intervals. It is also possible to determine a reference value before each measurement. In this embodiment of the method, the correction step is preferably performed when the response signal exceeds or falls short of a limit value.

In another preferred embodiment of the method, a response signal of a disturbed liquid-transformer system, i.e., a liquid-transformer system with a certain type of clogging, for example, is preset as a reference value. This reference value, in turn, may be stored. The reference value can be determined, in turn, by measuring a response signal in a malfunctioning liquid-transformer system and storing it in a control means. In this preferred embodiment of the method, the correction step is preferably performed when the response signal lies within a preset deviation from the reference value. This means that the response signal substantially corresponds to the reference value here so that it can simultaneously be detected which type of disturbance has occurred, e.g., whether there is a partial or a complete clogging. Preferably, several reference values are stored in dependence on occurring disturbance types. Different reference values are stored, for example, for a complete clogging, a partial clogging or a drop clinging to the tip of a pipetting or dispensing means. Thus, it is possible to simultaneously detect the type of disturbance on the basis of the response signal.

The reference value, which may be the reference value of an operative or a malfunctioning liquid-transformer system of a certain type of disturbance, may also be detected by means of substitute models of the liquid-transfer device. It is particularly possible to detect reference values by means of computer simulations.

Preferably, a correction step will only be performed when the limit value has been exceeded/fallen short of or a response signal within a preset deviation from the reference value has occurred repeatedly, e.g., within a preset period of time, or in immediate succession. Thus, a correction step is performed in dependence on statistics.

The liquid delivery pump may also be a pump such as a HPLC pump, for example. In this case, a response signal can be measured directly at the pump or by a succeeding liquid-transformer system. The reference value itself may be variable as to time (f(t)), the variation being calculated or generated as a function of a further measured signal, such as, e.g., as a function of the relation of acetonitrile/water in case of a HPLC pump. By means of the method according to the invention, it is thus possible to determine the composition of the HPLC liquids, e.g., in connection with a preset gradient.

It is also possible, for example, to detect the state of a valve by means of the method according to the invention by the use of an additional liquid-transformer system. As soon as the valve has been opened, there is liquid in a portion located behind the valve in flow direction. Thereby, the response signal changes. Thus, the operability of a valve can be checked by means of the method according to the invention. This is particularly advantageous with microsystem chips.

The reference value, e.g., is a value (e.g., input impedance in case of a frequency), a combination of values (e.g., input impedance in case of several frequencies), a certain limited range of values (partial spectrum (e.g., input impedance between 1000 and 3000 Hz)), an entire spectrum and/or a mathematical function. The reference value can be regarded as a value, i.e., as a single curve, for example, or as a tolerance range, i.e., between two curves, for example. Preferably, the response signal is determined in a first step at a single frequency for determining the error occurred as exactly as possible. This frequency is included in the spectrum of the reference value. If the response signal obtained by this frequency does not permit a clear statement as to the error, the response signal is preferably determined with a combination of frequencies, ranges of different frequencies (partial spectra) or in correspondence with the reference value over the entire spectrum. Thereby, it is possible to detect the exact error in question—if necessary, in several steps.

The correction step may consist in performing a cleaning step or dabbing a dispensing or pipetting tip. Another example for a correction step is to stop the liquid delivery with or without outputting a corresponding signal to the user. Then, in dependence on the detected error, for example, the user may execute a cleaning, a new adjustment or the like at the liquid delivery device. Further, the detected error value may also be stored. Such a storing may be used for statistical evaluations in order to check whether the detected type of error really corresponds to the actual type of error, etc. It is also possible, for example, to neither change the delivered quantity nor perform a cleaning or the like in a correction step but rather merely store the detected error and continue the liquid delivery procedure without any changes. The storing may be performed, for example, with respect to a particular well so that, in a future examination of this well, it is known that errors have occurred when delivering liquid into this well and thus, the measured results might be falsified. Depending on the type of the error occurred, it may be relevant for all the succeeding wells or also for the specific well only.

The method may be carried out, e.g., at regular intervals during a procedure of filling titer plates or other sample carriers. It is further possible to continuously carry out the method according to the invention during the entire filling procedure. This is a particularly preferred embodiment of the method. Preferably, the state of the liquid-transformer system is measured by the signal by which the liquid delivery device is simultaneously operated. To this end, a signal is chosen which is suitable for exciting the liquid-transformer system and includes the frequencies at which the response signal is to be measured. In the simplest case, a sinusoidal signal can be used. To guarantee a corresponding actuation of the transformer, the excitation signal comprises a sufficient amplitude. Thus, it is possible to operate the liquid delivery device as well as to simultaneously carry out a function monitoring with one and the same signal.

The method according to the invention has the advantage that no additional sensor for monitoring the operability of the liquid delivery device is required. The monitoring is rather performed directly via a preferably reversible electromechanical transformer such as a piezoactuator of a micropump, which simultaneously operates the liquid delivery device and performs the operability monitoring as well. Further, a plurality of different errors can be detected by the method according to the invention. Apart from the fact that air or gas bubbles can be detected in the liquid, cloggings, efflorescences and depositions are detectible as well. As described above, it is also possible to detect a dipping of the liquid delivery tip in a liquid. By means of the method according to the invention, it is particularly possible to detect physical changes of the liquid. A change of viscosity caused by temperature variation, for example, is detected by means of the method according to the invention. By means of the method according to the invention, it is also possible to detect that a liquid drop clings to the liquid delivery tip, since the mass of this liquid drop is a part of the mass of the liquid-transformer system and thus, a response signal is produced that differs from the reference value.

The liquid acted upon by the transformer is preferably disposed in a chamber, particularly a chamber of a micropump. Typically, the chamber of a micropump comprises an inlet opening of small diameter for supplying liquid into the chamber. Further, the chamber of a micropump comprises an outlet opening that also has a small diameter. By generating pressure in the chamber by means of a piezoactuator, liquid is ejected from the outlet opening. By such pumps, it is possible to eject minimum quantities of liquid in the range of a few nanoliters or less. By micropumps, single drops or a larger quantity of liquid can be ejected.

In another preferred embodiment of the invention, the generation of the excitation signals as well as the reception of the response signal is effected by means of the transformer. This can be performed by the fact that the transformer generates a pulse as an excitation signal, is switched to reception mode and is thus able to receive the response signal of the system. It is then required, however, that the excitation pulses are very short since the response signal comes very fast because of the small size of the system.

In a particularly preferred embodiment, the delivery of the excitation signal and the reception of the response signal is effected simultaneously or may overlap in time at least partially. With an electric or electromechanical transformer such as a piezoactuator, this may be effected by applying a voltage to the transformer. Then, the response signal of the liquid-transformer system is the current flowing in the transformer, for example. Thus, the response signal is a measure for the "resistance" the transformer meets upon moving the liquid. From this response signal, i.e., the "transformer resistance", information on a disturbance such as an air bubble, a clogging of the nozzle or a covibration of a drop hanging in a nozzle etc. can be obtained. Preferably, the response signal is determined by means of the impedance, the capacitance and/or the admittance of the liquid-transformer system. Preferably, the reference value is determined by means of the impedance, the capacitance and/or the admittance of the liquid-transformer system as well. By means of the electric impedance, e.g., it is easily possible to detect changes in the phase shift between current and voltage, occurring at malfunctions. The input impedance, the input admittance or the input capacitance can be used for measuring.

After having detected a malfunction by comparing the reference value with the response signal, a cleaning cycle, for example, can be carried out as a correction step. A cleaning cycle, for example, is the continuous delivery of a large liquid quantity. This effects the flushing of air bubbles, depositions and the like from the chamber. If, for example, a change of the viscosity of the liquid is detected by the method according to the invention, a change of the excitation signal of the electromechanical transformer can be effected-as a correction step as well so that an adaptation of the delivered liquid quantity to the changed viscosity of the liquid is effected. This results in that a constant drop volume can also be produced with changing viscosities of the liquid. Corresponding excitation signals in dependence on the viscosity are preferably deposited in the memory means.

The different disturbances (air bubbles, depositions, dipping into a liquid) cause a different response signal. Since the response signals can be differentiated, it is possible to detect the type of error on the basis of the response signal. It is possible to directly detect the type of error by a suitable control means in which the different values of the response signals with respect to an error type are stored. This results in that by means of the control means, the reactions can be different in dependence on the type of error. If an air bubble was detected in the chamber, the chamber could be flushed, for example. If, for example, a drop clinging to the liquid delivery tip was detected, it would be possible to simply and effectively rectify the error by dabbing the liquid delivery device on an absorbent cloth or the like.

Further, the method according to the invention is also suitable, e.g., for the monitoring of pumps, particularly HPLC pumps. Here, it is possible not only to monitor the operability of the pump but also to control the pump itself by means of the method according to the invention. When the method according to the invention is employed in connection with pumps, particularly HPLC pumps, a monitoring of the gradient in the HPLC pump is possible. Here, a change of the composition of the liquid because of contamination or the like is detected as a malfunction. As a correction step, the respective pumps of the liquids can here be controlled differently to readjust the gradient.

In a preferred embodiment of the method according to the invention, it is possible to not only provide the excitation signal as a single excitation frequency but as a signal comprising several excitation frequencies, e.g., as a square wave signal. Thereby, it is possible to accommodate several points, partial spectra or an entire spectrum of the response signal. Then, for example, different combinations of frequencies or signals can also be significant for different types of errors.

For exciting the liquid-transformer system for receiving the response signal, it is further possible not to use the same means as that producing the signal acting upon the transformer but to provide different means. The excitation of the liquid-transformer signal, for example, may be effected electrically or magnetically via a transformer and the acquisition of the response signal can be effected mechanically or optically. Furthermore, it is possible that the transformer for the liquid delivery and the function monitoring is not identical.

Further, the invention relates to a liquid delivery device being particularly suitable for delivering minimum quantities. The liquid delivery device comprises a liquid receiving portion, such as, for example, the chamber of a micropump. Further, the liquid delivery device comprises a transformer acting upon the liquid provided in the liquid receiving portion. The transformer is, for example, a reversible transformer, preferably an electromechanical transformer, such as a piezoactuator. In further preferred embodiments, it is, for example, a magnetorestrictive transformer. Further, the liquid delivery device comprises a control means connected with the transformer. The control means serves to excite the transformer with an excitation signal. Further, the control means preferably also serves to acquire a response signal of the liquid-transformer system. It is a response signal to the excitation signal. Further, the control means serves to compare a reference value with the response signal. As described above, the reference value may be, for example, a value or a combination of values etc. of an operative or a malfunctioning system. Preferably, it is stored in the control means.

The liquid-transformer system comprises the transformer and the liquid receiving portion. Substantial for the invention is that the liquid receiving portion is also considered to be a portion having influence upon the response signal.

Further, all the other covibrating portions of the liquid-transformer system have influence upon the response signal.

In a particularly preferred embodiment, the transformer simultaneously acts as an actuator and as a sensor. As described above with respect to the method according to the invention, the generation of the excitation signal as well as the reception of the response signal may be effected with a time offset or preferably simultaneously or in an overlapping manner. Here, it is particularly preferred to determine the input impedance, the input capacitance and/or the input admittance of the transformer. If necessary, the response signal is carried out by means of a software or the comparison between the response signal and the reference signal is made by means of a software to be able to detect even extremely minor changes. With droplets clinging to the nozzle or with partial cloggings, for example, the input impedance changes are only extremely small. In this case, it is advantageous to favorably select the frequency at which the comparison of the response signal with the reference value is made in dependence on the liquid-transformer system. Particularly the measuring parameter has to be chosen advantageously. The phase values have proven to be advantageous measuring parameters.

The liquid delivery device according to the invention is particularly suitable for carrying out the above method. The respective components of the liquid delivery device according to the invention and particularly the control means are configured such that they are suitable for carrying out the above method and particularly the preferred embodiments.

Hereinafter, the invention is described in detail with respect to preferred embodiments with reference to the accompanying drawings.

Figure 3:
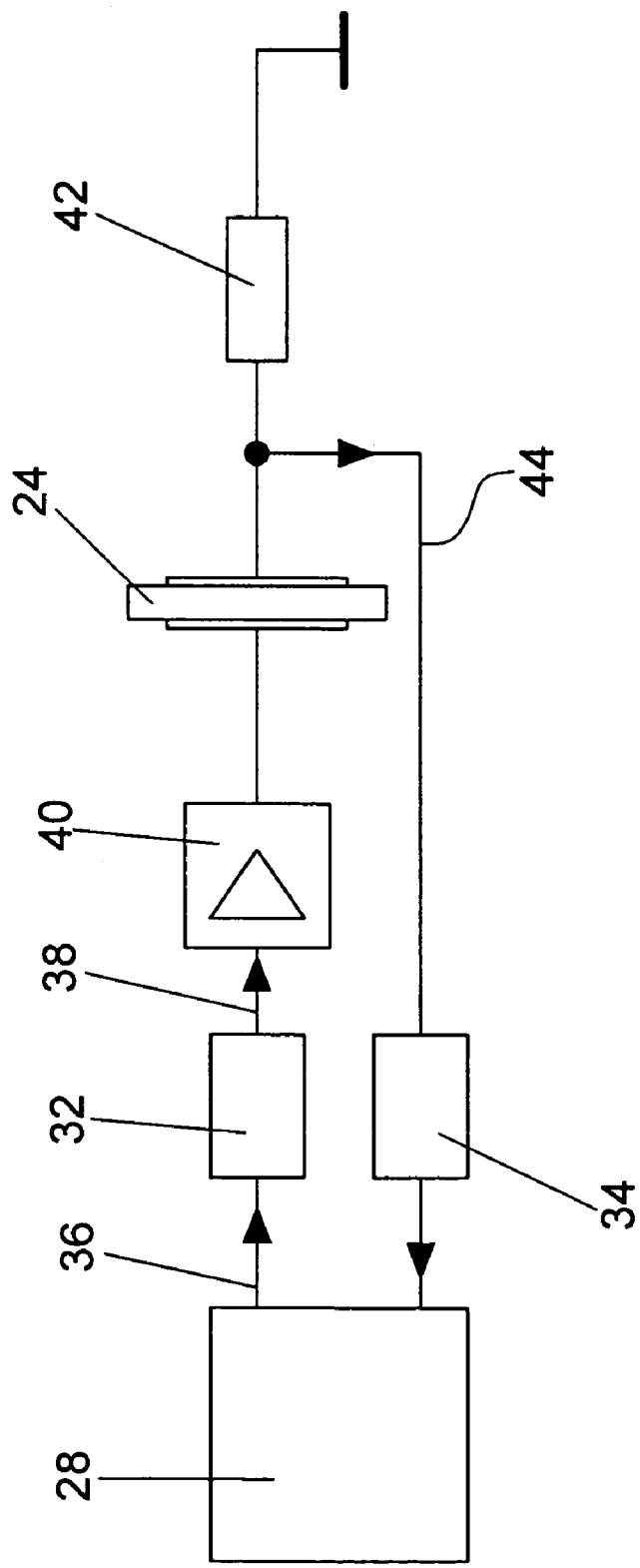
Figure 4:
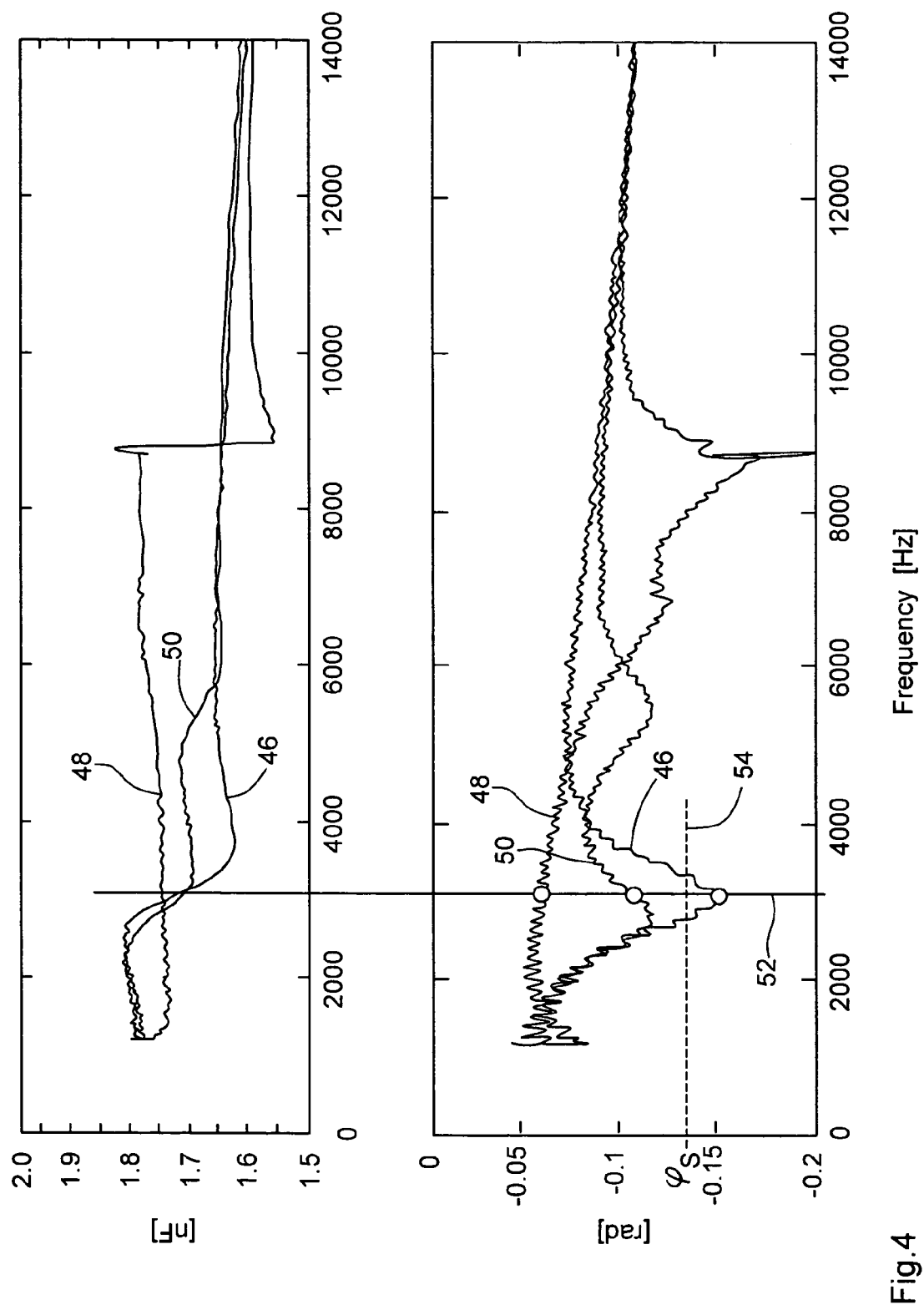
Figure 5:
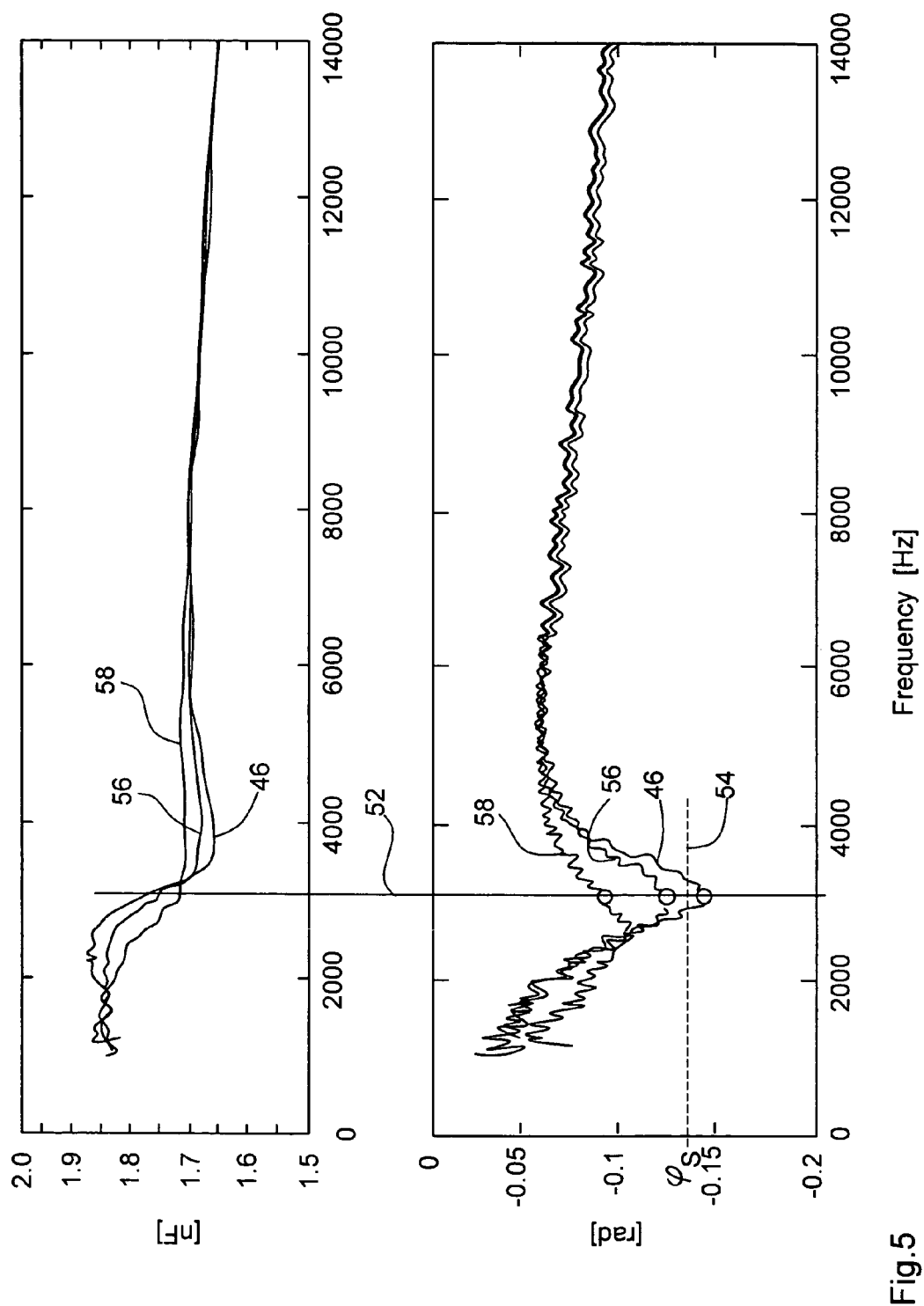

In the Figures:

FIG. 1 shows a schematic front view of a liquid delivery device,

FIG. 2 shows a schematic lateral view of the liquid delivery device illustrated in FIG. 1, FIG. 3 shows a schematic circuit diagram for carrying out the method according to the invention, FIG. 4 shows signal courses of the reference value and the response signal upon occurrence of an air bubble, and FIG. 5 shows signal courses of the reference value and of response signals upon occurrence of a clogging.

In the illustrated embodiment, a dispensing device 10 is illustrated as a liquid delivery device. It comprises a chamber 12 filled with sample liquid. Via a channel 14, the chamber is connected with a reservoir. At a dispensing tip 16, an outlet opening 18 is connected with the chamber 12 via a capillary 20.

A rear wall 22 of the chamber 12 has a flexible configuration. A piezoactuator 24 is provided adjacent to the rear wall 22. Via a line 26, the piezoactuator is connected with a control means 28. The piezoactuator 24 can be activated by the control means 28. By activating the piezoactuator, pressure is exerted on the flexible rear wall 22 of the chamber 12. Because of the pressure increase in the chamber 12, droplets 30 are ejected from the outlet opening.

The control means 28 preferably is a computer (FIG. 3). The function of the control means 28 may as well be taken over by a computer carrying out other objects as well. To this end, the computer 28 comprises a transformer, e.g., a transformer card, consisting of a D-A converter 32 and an A-D converter 34. Thus, the D-A converter 32 converts a signal 36 produced by the computer 28 into an analogous signal 38 amplified by an amplifier 40 and subsequently supplied to the piezoactuator 24. The signal 38 is a signal including the excitation signal. The voltage of the signal 38 is either selected such that only the operatibility monitoring is performed or a droplet delivery through the outlet opening 18 of the pipetting tip 16 (FIG. 1) is simultaneously performed as well.

By means of a measuring resistor 42, a response signal 44 is supplied to the control means 28 via the A-D converter 34. The response signal is the response signal of the liquid-transformer system, i.e., the response signal particularly caused by the transformer 24 as well as by the liquid in the chamber 12 and all the liquid communicating therewith (e.g., capillaries 20, drops at the nozzle etc.) The other mechanical parts of the liquid-transformer system, such as, for example, the diaphragm and the capillary 20, have an influence on the response signal. In the operational state, i.e., during the monitoring of the operability, the response signal 44 is the response signal. Before, the reference value is produced with the same circuit illustrated in FIG. 3 and stored in the control means 28. Upon producing the reference value, it must be paid attention to that there are no contaminations, air bubbles and the like in the chamber 12 or capillaries 20.

The diagram illustrated in FIG. 4 shows the complex input capacitance of a dispenser as a function of the frequency. Here, the upper diagram shows the amount of the capacitance as a function of the frequency and the lower diagram shows the phase of the capacitance as a function of the frequency. Both diagrams are obtained from the signals by Fourier transform. Of course, further mathematical moment analyses and transforms such as, for example, Laplace analyses, moment analyses, correlation analyses, wavelet analyses etc. are possible as well. In the experiment illustrated herein, water was used as liquid. The excitation voltage supplied to the transformer 24 was 10 Volt. Thus, no liquid was delivered because liquid is only delivered as of a voltage of about 25 V. In an operative liquid-transformer system, i.e., without disturbances, such as air bubbles in the chamber 12, the curve 46 is produced. Thus, this curve can be regarded as reference value. When there is an air bubble in the region of the capillary 20 connecting the outlet opening 18 with the chamber 12, the curve 46 is produced. Thus, this curve can be regarded as a reference value. In case of a small air bubble in the chamber 12, the curve 50 is produced. The resonance frequency illustrated by a line 52 amounts to about 3000 Hz in the illustrated example.

In order to detect a disturbance—an air bubble in the present example—a liquid-transformer system is excited by a signal including the frequency to be analyzed. In the present example, the signal may include a frequency of about 3000 Hz corresponding to the line 52. Subsequently, the complex capacitance from the time signal is analyzed by Fourier transform. At least, this analysis must be effected at the frequency of interest 52. At the resonance frequency (line 52), the curve 46, i.e., the curve of an operative non-disturbed liquid-transformer system is below a limit value $\phi_s$ illustrated by the line 54. The phase angles of the two curves 48,50 representing the response signals in case of disturbing air bubbles lie above the limit value $\phi_s$. As is clearly apparent from the lower diagram of FIG. 4, the phase shifts of the two curves 48,50 also differ strongly from each other. Thus, it is possible to detect the type of the disturbance on the basis of the amount of the phase shift. Then, the control means 28 may perform a cleaning cycle, a dabbing of the dispenser tip 16 or the like in dependence on the type of disturbance.

Two diagrams corresponding to those of FIG. 4 are represented in FIG. 5. The experiment evaluated by means of the diagrams in FIG. 5 is an intentionally caused clogging of the capillary 20 (FIG. 1). The curve 46 corresponds to the curve 46 in FIG. 4 and thus represents the response signal of an operative liquid-transformer system without clogging or other disturbance and thus, it can be regarded as a reference value. The curve 56 represents a locking of the capillary by 2.6% of the cross-sectional area. The curve 58 represents a locking of the capillary 20 by 16% of the cross-sectional area. At the same limit value $\phi_s$ and the same resonance frequency, which are illustrated by the lines 52 and 54, respectively, the reference value (curve 46) is compared with the response signal (curve 56 or 58) again. Therefrom, it is clearly apparent that the clogging can be definitely detected. On the basis of the amount of the phase shift, even the size of the clogging can be detected. Thus, e.g., a value can be stored where the dispensing must be interrupted since the clogging is to large to be remedied by a flushing procedure.

As can be seen from the diagrams in FIGS. 4 and 5, the signals of malfunctioning and operative liquid-transformer systems not only differ in the resonance frequency but also in other frequencies. Therefore, it is also possible to read out other frequencies and draw conclusions therefrom as to the type of disturbance. Further, response signals of several frequencies can be monitored simultaneously and from a combination of several frequencies, with respect to a limit value or other reference values, conclusions as to the type of error can be drawn. Thereby, for example, a detailed determination of the type of error as well as an increase in the security that the right error has been determined is possible. In FIG. 4, for example, considerable deviations of the capacitance and the phase, respectively, can also be detected at a frequency of about 9000 Hz.

The invention claimed is:

1. Method for monitoring the operability of a liquid delivery device adapted to be employed for delivering chemical and/or biological liquids, comprising the step of:
   supplying a liquid receiving portion and a transformer acting on the liquid in the liquid receiving portion,
   exciting the transformer with an excitation signal,
   acquiring a response signal caused by the excitation signal of the liquid-transformer system,
   comparing the response signal with a reference value, and
   performing a correction step depending on the result of the comparison,
   wherein he excitation signal also serves as a signal by which the liquid delivery device is simultaneously operated to deliver liquid.

2. The method of claim 1, wherein the reference value is the response signal of the operative liquid-transformer system.

3. The method of claim 2, wherein the reference value is determined by measuring the response signal of an operative liquid-transformer system at or near a resonance frequency.

4. The method of claim 1, wherein the correction step is performed when a limit value ($\phi_s$) is exceeded or fallen short of.

5. The method of claim 1, wherein the reference value is the response signal of a malfunctioning liquid-transformer system.

6. The method of claim 5, wherein the reference value is determined by measuring the response signal of a malfunctioning liquid-transformer system at or near a resonance frequency.

7. The method of claim 1, wherein the correction step is performed when the response signal lies within a preset deviation of the reference value.

8. The method of claim 1, wherein different reference values are stored in the control means in dependence on the type of disturbance occurring.

9. The method of claim 1, wherein the reference values are determined by means of a mathematical substitute model of the liquid delivery device or by means of computer simulation.

10. The method of claim 1, wherein the correction step is performed after the limit value ($\phi_s$) has been exceeded/fallen short of repeatedly or a response signal within the preset deviation from the reference value has occurred repeatedly.

11. The method of claim 1, wherein the reference value is a function in dependence on time.

12. The method of claim 1, wherein the liquid onto which the transformer acts is disposed in a chamber and/or capillary.

13. The method of claim 1, wherein the response signal and/or the reference value are determined by means of the impedance of the liquid-transformer system.

14. The method of claim 1, wherein the response signals are determined by means of a mathematical transform.

15. The method of claim 14, wherein the amplitudes and/or phase shifts of the response signals are compared.

16. The method of claim 1, wherein the type of error is determined on the basis of the response signal.

17. The method of claim 1, wherein the excitation signal and the response signal are overlaid on each other in time at least partially.

18. A liquid delivery device, particularly for the delivery of minimum quantities of chemical and/or biological liquids, comprising a liquid receiving portion, a transformer acting on the liquid, and a control means connected with the transformer, for exciting the transformer with an excitation signal, for acquiring a response signal of the liquid-transformer system and for comparing a reference value with the response signal,
   wherein the response signal sent by the liquid-transformer system is caused by the excitation signal, and wherein the excitation signal also serves as a signal by which the liquid delivery device is simultaneously operated to deliver liquid.

19. The liquid delivery device of claim 18, characterized in that the liquid transformer system producing the response signal comprises the transformer as well as the liquid in the liquid receiving portion.

20. The liquid delivery device of claim 18, characterized in that a reference value is stored in the control means.

21. The liquid delivery device of claim 20, characterized in that the reference value is stored in dependence on the liquid properties and/or liquid quantity on which the transformer acts.

22. The liquid delivery device of claim 18, characterized in that in the control means, response signals are stored each of which has a type of error allocation thereto.

23. The liquid delivery device of claim 18, characterized in that the transformer acts as an actuator and as a sensor at the same time.

* * * * *

UNITED STATES PATENT AND TRADEMARK OFFICE
CERTIFICATE OF CORRECTION

PATENT NO. : 7,096,710 B2
APPLICATION NO. : 10/483083
DATED : August 29, 2006
INVENTOR(S) : Hartwig Preckel et al.

It is certified that error appears in the above-identified patent and that said Letters Patent is hereby corrected as shown below:

On Title Page,
Item (73) Assignee: Evotec OAI AG, Hamburg (DE)

Signed and Sealed this

Ninth Day of January, 2007

JON W. DUDAS
*Director of the United States Patent and Trademark Office*